United States Patent
Soini

(10) Patent No.: US 6,177,277 B1
(45) Date of Patent: *Jan. 23, 2001

(54) FLOW FLUOROMETRIC METHOD

(75) Inventor: Erkki Soini, Krypingintie 20, Fin-21610 Kirjala (FI)

(73) Assignee: Erkki Soini, Kirjala (FI)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/817,797
(22) PCT Filed: Jan. 3, 1996
(86) PCT No.: PCT/FI96/00003
§ 371 Date: May 13, 1997
§ 102(e) Date: May 13, 1997
(87) PCT Pub. No.: WO96/22521
PCT Pub. Date: Jul. 25, 1996

(30) Foreign Application Priority Data

Jan. 16, 1995 (FI) .................................. 950174

(51) Int. Cl.$^7$ .................................... G01N 21/64
(52) U.S. Cl. .................. 436/63; 436/172; 356/72; 356/73
(58) Field of Search ................ 422/81, 82.08; 436/63, 172; 356/72, 73

(56) References Cited

U.S. PATENT DOCUMENTS

| | | | |
|---|---|---|---|
| 4,421,860 | 12/1983 | Elings et al. | 436/518 |
| 4,676,640 | * 6/1987 | Briggs | 356/317 |
| 4,734,578 | * 3/1988 | Horikawa | 356/444 |
| 5,028,545 | 7/1991 | Soini | 436/501 |
| 5,034,613 | 7/1991 | Denk et al. | . |
| 5,117,466 | * 5/1992 | Buican et al. | 356/73 |
| 5,196,709 | 3/1993 | Berndt et al. | . |
| 5,198,369 | * 3/1993 | Itoh et al. | 436/534 |
| 5,308,990 | 5/1994 | Takahashi et al. | . |
| 5,518,883 | 5/1996 | Soini | 435/6 |
| 5,523,573 | 6/1996 | Hänninen et al. | 250/459.1 |
| 5,674,698 | 10/1997 | Zarling et al. | 435/7.92 |
| 5,815,262 | * 9/1998 | Schrof et al. | 356/318 |
| 5,891,738 | * 4/1999 | Soini et al. | 436/501 |
| 5,949,532 | * 9/1999 | Schrof et al. | 356/73 |

FOREIGN PATENT DOCUMENTS

| | | |
|---|---|---|
| 442025 | 8/1991 | (EP) . |
| 0 587 008 A1 | 3/1994 | (EP) . |
| WO 94/07142 | 3/1994 | (WO) . |
| WO 94/11735 | 5/1994 | (WO) . |
| WO 94/16313 | 7/1994 | (WO) . |

* cited by examiner

Primary Examiner—Jeffrey Snay
(74) Attorney, Agent, or Firm—James C. Lydon

(57) ABSTRACT

This invention is related to a flow fluorometric device and method employing a two-photon excitation and/or confocal optical set-up. The optical set-up of this invention is optimal for counting small fluorescent biological particles. The active focal volume is diffraction-limited and consequently much smaller than the volume of the flow channel. The excitation and detection concept has been found very efficient for rejection of the background signal. An objective lens with large numerical aperture for focusing the laser and for collecting the fluorescence is used and this restricts the active volume of measurement to a diffraction-limited volume which approximately corresponds to a volume of femtoliter. This volume is significantly smaller than the detection volume of ordinary flow cytometry.

7 Claims, 1 Drawing Sheet

FLOW FLUOROMETRIC METHOD

A flow cytometer is a device which is now widely used in routine diagnostics and research laboratories for analyzing and classifying cells and other particles. The cells are in liquid suspension and this suspension is pumped through a thin capillary cuvette and a laser beam is focused to the stream at a 90° angle in relation to the laser beam and detection objective lens. The laser beam can also be focused on the stream outside the capillary orifice. The sample suspension is kept in the focus of the laser beam using hydrodynamic focusing which forces the cells to flow along the centre of the axis of the capillary cuvette. Flow cytometry has recently been reviewed in many articles and e.g. by Salzman & al. in: Flow Cytometry and Sorting, Second Edition, M. R. Melamed, T. Lindmo, M. L. Mendelsohn, Eds. Wiley & Sons, Inc., New York, 1990, pp. 81–107.

The cells are normally stained with one or several fluorescent dyes or fluorescent biomolecules e.g. antibodies and flow cytometers are used for measurement of fluorescence and light scattering emitted during a course of laser excitation and these parameters are used for scoring the cells according to their characteristic features e.g. immunochemical features indicated by the fluorescent dye. The scattering signal normally indicates the size of the cell. A flow cytometer can be made for analyzing the cells or alternatively for physical separation (sorting) of cells. In the latter case the flow cytometer is combined with an electrostatic deflection device that brings the liquid droplets, which carry an electrostatic charge and include a cell being ejected from the orifice, to different cuvettes for further analysis.

The flow speed in an ordinary flow cytometer is 10–100 cm/s. Consequently, each cell is exposed by the laser beam for about 10–100 microseconds. The photon burst resulting from the fluorescence emission is detected by a photodetector and an electric signal will be obtained from the detector having an amplitude which is directly proportional to the amount of the fluorescent dye in the cell.

The electric signals will be analyzed and registered and normally a histogram will result showing the number of cells versus fluorescence intensity.

The precision, sensitivity and reliability of flow cytometry is reduced by different factors including non-specific fluorescence, autofluorescence of the cells, fluorescence of the optics and noise generated in the photo-detectors. The sources of interference cause variation and randomly occurring signals. As a consequence, an ordinary flow cytometer is not capable of resolving small amounts of specific cells within the population of normal cells and cells that constitute less than 1/1000 of the main population are not detectable. Examples of analysis of such "rare events" include the screening for cancer cells in the blood circulation for detection of minimum residual disease and screening of foetal erythroblasts in maternal blood circulation for early detection of genetic abnormalities. Another example is fast detection of low amounts of small cells e.g. bacteria in liquor or blood without cultivation. Erythrocytes and bacterial cells are small (1–5 $\mu$m) and they are not resolvable with ordinary flow cytometers without a strong unspecific interference. The reliable and fast detection of human and bacterial cells referred above has great potential in medicine.

Detection of "rare events" or small particles with conventional flow fluorometry is hampered by background fluorescence and scattering and it is very difficult to discriminate false signals from true signals. This invention is related to an improved device and methodology for detection of rare events or small particles in biological fluids. The term "particle" used in the text refers to any biological particle including mammalian cells, blood cells, bacterial cells, cell organelles and viruses.

BACKGROUND OF THE INVENTION

The background art of this invention is covered by many articles dealing with flow fluorometry of small particles, confocal optical microscopy, two-photon excitation, fluorescence correlation spectroscopy and single molecule detection. As background art of this invention we list the following articles relative to sensitive flow fluorometry:

Two-Photon Excitation

Denk, W., Strickler, J., and Webb, W. W. Two-photon laser microscopy. U.S. Pat. No. 5,034,613, 1991.

Lytle, F. E., Dinkel, D. M., and Fisher, W. G. Trace-Level Quantiation Via Time-Resolved Two-Photon-Excited Fluorescence. Appl. Spectrosc. 47(12):2002, 1993.

Denk, W, Strickler, J. H., and Webb, W. W. Two-photon laser scanning fluorescence microscopy. Science. 248:73, 1990.

Sepanlak, M. J. and Yeung, E. S. Laser Two-Photon Excited Fluorescence Detection for High Pressure Liquid Chromatography. Anal.Chem. 49(11):1554–1556, 1977.

Wirth, M. J. and Fatunmbi, H. O. Very-High Detectability in Two-Photon Spectroscopy. Anal.Chem 62:973–976, 1990.

Flow Fluorometry and Cytometry

Nguyen, D. C. and Keller, R. A. Ultrasensitive laser-induced fluorescence detection in hydrodynamically focused flows. Journal of the Optical Society of America B 4(2):138, 1987.

Confocal Microscopy

Mathies, R. A. and Peck, K. Laser excited confocal microscope fluorescence scanner and method. Eur. pat. appl. 91300246.5(440 342 A3), 1991. GO1N 21/64.

Single Molecule Detection

Dovichi, N. J., Martin, J. C., Jett, J. H., Trkula, M., and Keller, R. A. Laser-Induced Fluorescence of Flowing Samples as an Approach to Single-Molecule Dectection in Liquids. Anal. Chem. 56(3):348, 1984.

Lee, Y., Maus, R. G., Smith, B. W., and Winefordner, J. D. Laser-Induced Fluorescence Detection of a Single Molecule in a Capillary. Anal.Chem. 66(23):4142, 1994.

Mathies, R. A. High Sensitivity Fluroerscent Single Particle and Single Molecule Detection Apparatus and Method. PCT/US90/02702(WO 90/14589), 1990, GO1N 21/64.

Mathies, R. A., Peck, K., and Stryer, L. Optimization of High-Sensitivity Fluorescence Detection. Anal.Chem, 62(17):1786, 1990.

Peck, K., Stryer, L., Glazer, A. N., and Mathies, R. A. Single-molecule fluorescence detection: Autocorrelation criterion and experimental realization with phycoerythrin. Proc.Natl.Acad.Sci. 86:4087, 1989.

Shera, E. B. Single molecule tracking. Eu. Pat. 88909172.4 (EP 0 381, 694 B1), 1988. GO1N 21/64.

Shera, E. B., Seitzinger N. K., Davis, L. M., Keller, R. A, Soper, S. A., Detection of single fluorescent molecules, Chem Phys Letter 23:553–557, 1990.

Fluorescence Correlation Spectroscopy

Dovichi, N. J., Martin, J. C., Jett, J. H., and Keller, R. A. Attogram Detection Limit for Aqueous Dye Samples by Laser-Induced Fluorescence. Science. 219:845, 1983.

Rigler, R. and Eigen, M. Method and device for assessing the suitability of biopolymers. PCT/EP/00117 (WO94/16313), 1994. GO1N 21/64.

OBJECTS OF THE INVENTION

The object of this invention is an improved method and device for flow fluorometry. The reliability and precision of flow cytometric analysis can be improved significantly with this invention. In particular the analysis of rare events and small size particles in biological suspensions comprising a large number of particles of different kinds and sizes, can be improved and the interferences typical for the ordinary flow cytometry can be reduced. In addition, this invention allows the use of a laser of lower power and less expense than in the ordinary flow cytometry typically used today.

DETAILED DESCRIPTION OF THE INVENTION

Figure 1:
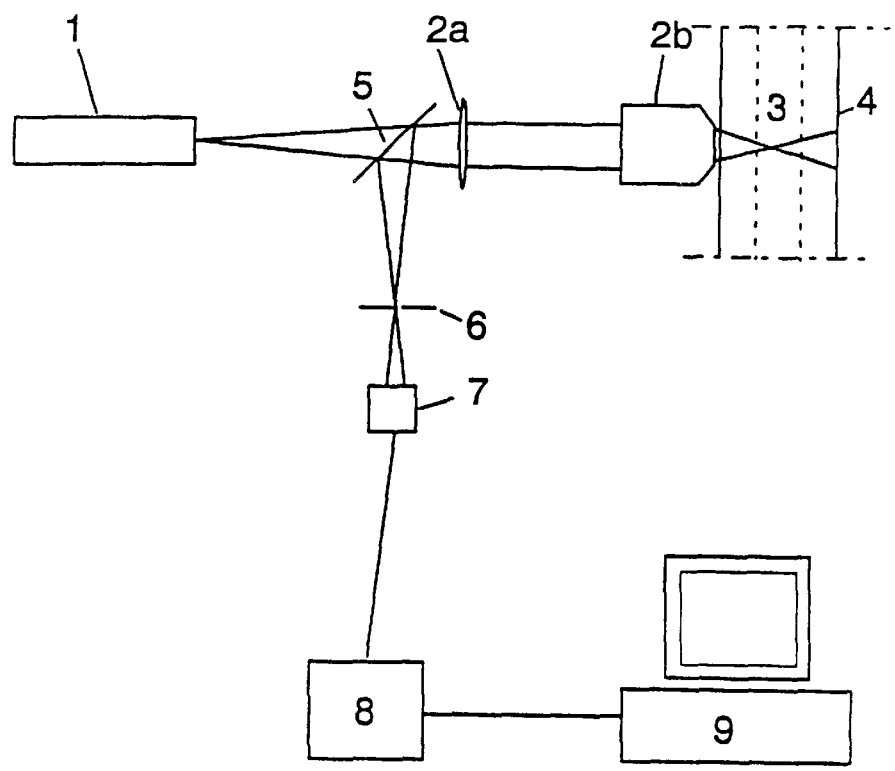
FIG. 1 is a functional diagram of the measuring system needed for the method of this invention.

The fluorescent dyes commonly used in flow cytometry provide high absorption of the excitation light and high quantum yield of the fluorescence emission. However, the sensitivity of detection is substantially limited by the illumination light scattering, background fluorescence of the optical parts and autofluorescence of the sample medium. In the ordinary flow cytometers the photon detector is optimized for very efficient collection of fluorescence emission from the entire cell and the illumination is performed with a focusing lens with relatively long focal length. This typical optical set-up provides a signal strong enough for commonly used photomultiplier tubes with relative low quantum efficiency being strongly dependent on the wavelength of the fluorescent emission and varying from 0.5% to 5%. For this reason, high-sensitivity flow cytometry often requires a powerful and expensive Argon-ion laser.

An essential difference between the ordinary flow cytometry and this invention is related to the focal volume of excitation and detection. In the ordinary flow cytometry the excitation is performed using a long focal length lens in order to assure homogenous illumination across the entire flow channel so that the variance of the illumination of different particles is minimal. Similarly, the detector is focused to the flow channel with a high numerical aperture objective lens, and a relative large aperture before the detector is used in order to optimize efficient light collection.

The device of this invention is based on the use of the confocal optical set-up and/or two-photon excitation. Both of these systems employ a high numerical aperture objective lens for excitation and detection. The focal volume of excitation is diffraction-limited and consequently much smaller than the volume of the flow channel.

The optical set-up of this invention is optimal for counting small fluorescent particles. The excitation and detection concept referred to above has been found very efficient for rejection of the background signal, which makes counting of small particles difficult in the ordinary flow cytometry. Using an objective lens with large numerical aperture for focusing the laser and for collecting the fluorescence, both of the optical set-ups restrict the active volume of measurement to a diffraction-limited volume which approximately corresponds to a volume of less than one femtolitre. This volume is significantly smaller than the detection volume of an ordinary flow cytometry. Both of these methods, and the related optical systems, discriminate very efficiently among all sources of background scattering and fluorescence which originate from outside the active diffraction-limited focal volume. Consequently, the signal to noise ratio is improved significantly.

An additional feature of this invention is related to signal analysis. In the ordinary flow cytometry the photomultiplier tubes are used in analogue mode, i.e. the amplitude of the pulse obtained from the photomultiplier tube is an integral of the photons detected during the illumination time of the particle. The pulse amplitude is proportional to the intensity maximum of the fluorescence. A pulse height analysis is normally used for discrimination of signals caused by background and for selecting those signals which are produced by particles of interest. In this invention, the signal analysis is not based on pulse height analysis, but on single photon counting and auto-correlation analysis of single photon events in the time domain.

Correlation analysis of single photon events requires a single photon counter with high counting efficiency. Recent introduction of the avalanche diode single photon counters has made the embodiment of this invention possible. Avalanche photon counters have very high quantum efficiency (up to 80%) for light emissions on a wide range of visible and near-infrared (NIR) light, and if used in flow cytometry, they contribute a signal rate comparable with photomultiplier tubes with much lower excitation intensity. This allows the use of less expensive lasers. The avalanche photon counters used in the device of this invention produce a burst of discrete pulses typically 10 ns long during the illumination time of the particle. These pulses are auto-correlated in the time domain and the correlation function is used for discrimination between specific particles and other non-specific signals including the background fluorescence and noise.

Realization of the Invention With the Confocal Principle

FIG. 1 is an example of the functional diagram of the measuring system needed for the method of this invention. It is realized with the confocal principle. The function of the device is as follows. The laser (1) is used for excitation of fluorescence and it is focused through a lens (2a) and a high numerical aperture objective lens (2b) to a hydrodynamically focused sample stream (3) inside a flow cuvette (4). The fluorescence signal from the sample is directed by a dichroic mirror (5) and a pinhole (6) to a detector (7). The detector (7) is connected to a signal analysis device (8). The signal analyzer converts the signals to numerical form and the results are processed in the computer (9), which also controls the hardware.

The principle of the confocal set-up is described below with reference to FIG. 1. Firstly, imaging of the point-like light source (1) to the focal plane (3) of the objective lens (2b) is described. Due to diffraction, a point-like light source forms an intensity distribution, which is characteristic to the optical system, in the focal plane. The intensity distribution is called the point spread function, which is determined in three dimensions. A normalized point spread function defines the probability S1 of how photons, radiated from a point-like light source, are distributed on the focal area (3); that is, the probability that the photons are absorbed to different parts of the sample volume.

A corresponding point spread function S2 can also be determined for the spatial distribution of the photons emitted from the focal point which reach the pinhole (6) in front of the detector (7). The value of this normalized function in the vicinity of the focal point defines the probability of the photons emitted from different points and hitting the pinhole (6).

In the confocal optical system that has been applied to the method and the device of this invention, the light source (1) and the pinhole (6) are focused to the same focal point (3). The probability that a photon radiated by a point-like light source (1) causes a fluorescence emission in the sample, and the emitted photon hits the pinhole (6), is described by the normalized product S1*S2 of the illumination and detection intensity distributions. The probability distribution thus derived, is three dimensional and is clearly more restricted than the one produced by conventional optics, especially in the axial direction. The fluid volume to be measured in a confocal system is considerably smaller than the one in a conventional optical system. When using an objective lens with a large numerical aperture (N.A.>0.5) and a confocal system, the active fluid volume is reduced to below a tenth of what is provided by an optical system of the ordinary flow fluorometry.

Realization of the Invention With Two-Photon Excitation

Confocal optical system discriminates very efficiently all background scattering and the fluorescence which originates from outside the active diffraction-limited focal volume. Consequently, the signal to noise ratio is improved significantly. In analysis of biological particles, however, the confocal system does not eliminate the light scattering from the particles themselves in the diffraction-limited focal volume. In order to solve this problem this invention employs the method of two-photon excitation.

In the ordinary flow cytometry and in the confocal concept described above, the fluorescent labels are single-photon excited, which means that the chromophores of the fluorescent label absorb light at a wavelength of the exciting light beam. Two-photon excitation provides even more efficient reduction of the background caused by scattering and autofluorescence than other concepts. Two-photon excitation is possible when, by focusing an intensive light source, the density of photons per unit volume and per unit time becomes high enough for two photons to be absorbed into the same chromophore. In this case, the absorbed energy is the sum of the energies of the two photons. According to the concepts of probability, the absorption of a single photon in a chromophore, is an independent event, and the absorption of several photons is a series of single, independent events. The probability of absorption of a single photon can be described as a linear function as long as the energy states that are to be excited are not saturated. The absorption of two photons is a non-linear process of the second kind. In two-photon excitation, the chromophore is excited only when both photons are absorbed simultaneously, that is approximately within a femtosecond. The probability of absorption of two photons is equal to the product of probability distributions of absorption of the single photons. The intensity of fluorescence emission, caused by two photons, is thus a quadratic process with respect to the photon density of illumination.

The properties of this invention's optical system have been described above with the response of the system to a point-like light source. A point-like light source forms, due to diffraction, an intensity distribution in the focal plane characteristic to the optical system (point spread function). When normalized, this point spread function is the probability distribution for the photons from the light source to reach the focal area. In two-photon excitation, the probability distribution of excitation equals the normalized product of the intensity distributions of the two photons. The probability distribution thus derived is 3-dimensional, and is clearly more restricted than that for single-photon excitation, especially in the axial direction. Thus in two-photon excitation, only the fluorescence that is formed in the clearly restricted 3-dimensional vicinity of the focal point is excited.

When a chromophore is two-photon excited and the excitation is restricted to the 3-dimensional vicinity of the focal point, then the scattering outside the vicinity of the focal point and from the optical components is reduced remarkably if compared to normal excitation. Furthermore, two-photon excitation decreases the background fluorescence outside the focal point, in the surroundings of the sample and in the optics. Since the exciting light beam must be focused onto as small a point as possible, two-photon excitation best suits the observation of small sample volumes and structures, which is also the situation in the method according to this invention.

The previously mentioned advantages of two-photon excitation are based on the fact that visible or near-infrared (NIR) light can be used for excitation in the ultraviolet or blue region. Similarly, excitation in the visible region can be achieved by NIR light. Because the wavelength of the light source is considerably longer than the emission wavelength of the chromophore, the scattering at the wavelength of the light source and the possible autofluorescence can be effectively attenuated by using low-pass filters (attenuation of at least 10 orders of magnitude) to prevent them from reaching the detector.

A common way to produce two-photon excitation is to use ultra-short laser pulses. During a short pulse, it is possible to achieve a sufficiently high energy density for two-photon excitation, but the average energy is kept low. It has been observed, though, that two-photon excitations can also be observed with continuous-wave laser illumination (DE-pat. appl. P 44 14 0940.9-42).

In our experiments, we have observed that a very high signal-to-background-ratio and good sensitivity can be reached with two-photon excitation and short-lived fluorescent labels. Suitable fluorescent labels for two-photon excitation are, for example, coumarine, rhodamine derivatives and phycobiliproteins.

In using the method of two-photon excitation, the coincidence condition of the laser pulse and the pulse from the photon detector can also be used to eliminate thermal noise from the photon detector. In this case, thermal noise becomes insignificant. The use of two-photon excitation is advantageous compared to any single-photon excitation method because scattering and background noise, especially caused by proteins and other macromolecules in the sample, is considerably lower. No fluorescence arises at the wavelength of the laser, nor can scattering caused by the laser beam reach the detector, because low-pass filters effectively block the wavelength of the laser.

Two-photon excitation can best be performed with pulse lasers. The short detection and auto-correlation time requires a pulsed laser with very high repetition frequency. Today, the laser suitable for this application is the titanium-sapphire femtosecond laser with pulse energy of 10 nJ and with pulse frequency of 76 MHz and with adjustable 700–900 nm wavelength. Less expensive pulsed lasers suitable for this application will likely be available in the near future. An example of this kind of development is the mode-locked 300 MHz pulsed diode laser (Laser Ionics Inc., Orlando, Fla., U.S.A.), lambda=825 nm, pulse energy 0,03 nJ, pulse width 1–20 ps. Another example is a new, not yet commercially available diode pumped CrLi-Sapphire laser with 80 MHz pulse rate, 30 fs pulse width, 0.5 nJ pulse energy and adjustable 820–900 nm wavelength.

Two-photon excitation can provide a diffraction-limited focal volume which is slightly larger than that of the confocal set-up, but clearly defined in three dimensions. The lower resolution is simply a consequence of using a longer excitation wavelength for two-photon excitation. However, the optical system for two-photon excitation can also be combined with a confocal set-up. By choosing an appropriate detector pinhole it is possible to optimize the size of the focal volume.

Signal Analysis

Figure 2:
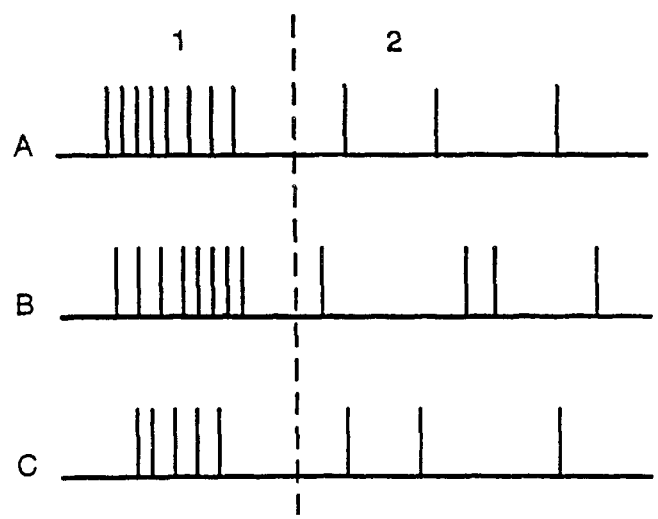
FIG. 2 presents an example of signals derived from the detector.

The duration of the single photon burst from the detector depends on the speed of the flow, dimension of the active focal volume and the size of the particle. The focal volume and its shape are defined by the point spread function of the confocal optics or two-photon excitation. The signals from the detector (7) in FIG. 1 are composed of single photon pulses, which are transformed to binary digital signals with a duration, for example, of 10 nanoseconds. FIG. 2 presents an example of pulses derived from the detector (7) in the time scales (A), (B) and (C). A particle of 1 $\mu$m diameter with the flow speed of 1 m/s remains for a time $t_m$=1 $\mu$s, later referred to as the transit time, under the excitation of the laser beam. The intensity of the laser beam, used for the excitation of label, is so high at the focal point (3) that it can nearly saturate the excited states. If the decay time of the fluorescent label is only 1 nanosecond, within the time interval $t_m$=1 microsecond, it can be excited and relaxed up to $10^3$ times under the excitation of a powerful laser beam. The number of photons observed by the detector, depends on the quantum efficiency of the label, the collection efficiency and the losses of the optics (2a, 2b, 4, 5 and 6) and the quantum efficiency of the photon detector (7). In practice, a detection efficiency of $10^{-2}$ can be obtained when using avalanche diode photon counters with 80% quantum efficiency. Within the transit time $t_m$, the detector (7) can detect one or many photons of the fluorescence emission which come from one particle. The photons appear as stochastic photon bursts within the transit time $t_m$ (section 1, FIG. 2). In addition to these bursts, many other stochastic signals may also be detected (section 2, FIG. 2). They originate from the background fluorescence caused by free molecules in the sample, from scattering and from thermal noise.

It is useful to adjust the laser intensity for optimal frequency of single photons to be detected during the photon burst from each kind of sample to be analyzed. If the laser intensity is too high, the rate of photons exceeds the counting speed of the detector and the Poisson distribution of the counts in the time domain will be distorted and consequently the discrimination between true signal and noise with auto-correlation analysis is not optimal. The excitation power is an adjustable parameter for the optimal photon emission rate from the samples in each particular application.

The avalanche diode photon counter may generate spontaneous after-pulsing with the probability of $10^{-3}$. Auto-correlating the signals with a threshold of 3 counts or higher eliminates the background caused by after-pulsing, but this is made at the cost of detection efficiency. By dividing the emission beam into two parts with a 50%/50% beam splitter for two separate photon counters and using a cross-correlator, it is possible to discriminate the after-pulses and to make the correlation time two-times shorter and to increase the count rate of the particles. The increased optical losses can be compensated with increased laser power.

The discrimination power between the background counts and the true counts from the particles can be enhanced further by the use of two or more different dyes for specific staining of the particles. The system can incorporate two or more fluorescence detectors respectively and the detectors used for fluorescence detection are, using appropriate spectral filters, tuned for the different wavelength bands corresponding to said different fluorescent dyes.

The use of high numerical aperture objectives and detection angles as large as possible is advantageous to the described methodology. If the detection aperture is doubled and thus each emitted photon has twice the probability to reach the detector, the increase in detection probability with the auto-correlation limit of N photons is $N^2$. This can also be achieved by using two or more objective lenses focused to the same focal point to collect the emitted photons at one or more detectors. The use of, for example, two objective lenses opposite to each other and two detectors increases the probability of detection by a factor of two.

The correlation analysis of the single photon counts can include both auto-correlation analysis and cross-correlation analysis. The auto-correlation analysis is based on registration of the time intervals between the photon counts from each detector. Application of the correlation analysis for two or several independent photon detectors is called cross-correlation. The emitted photons from the true particles, detected by one or several detectors during the transit time of the particle, can correlate in the time domain and within the following correlation parameters: correlation time, correlation thresholds in minimum a number of counts per detector, coincidence threshold defined for the condition of coincident counts from independent detectors. These correlation parameters are adjustable for optimal discrimination of non-specific photon counts.

Since the dimension of the active focal volume in the direction of the flow is very small, the information about correlated counts can also be used for determination of the duration of the transit time of each particle and consequently for determination of the approximate size of the particle. In study of small biological particles this method is useful for discriminating the non-specific fluorescence signals due to large particles in the same suspension.

The device performing the correlation analysis for single photon bursts can be an electronic logic circuit which gives an out-put signal if a pre-set number of single photon counts from each detector arrives within a pre-set period of time. The circuit may also perform more complex correlation functions or the circuit may be replaced by special computing software which is loaded into a dedicated signal processor or onto a conventional computer.

Ordinary flow cytometric analysis normally combines measurement of several parameters simultaneously. Most common is the combination of fluorescence and forward scattering. The scattering signal is used to evaluate the size of the particle. A cytogram shows the distribution of fluorescence intensity vs. scattering intensity for each particle.

The method of this invention allows the measurement of the scattering signal under similar principles typical for ordinary flow cytometers. However, small particles which are of special interest in the application of this method, provide very weak scattering signals and the signals give limited information about the sizes of the particles. Two alternative methods are now proposed for improving size determination.

The first alternative method is based on time distribution analysis of the single photon bursts from the particles. In case of large particles (10 $\mu$m), only a small part of the particle is excited by the diffraction-limited focal point in the confocal or in the two-photon excitation set-up. Consequently, these large particles remain under excitation for a much longer time than small particles and the burst of auto-correlating counts is longer. Analysis of the length of the burst offers a method of discriminating between small and large particles.

Another method for size determination is based on the use of a method called "Flying Light Scattering Indicatrix" (later "FLSI") which means determination of the angular dependency of the intensity of light scattered by a moving individual particle i.e. the light scattering pattern (V. P. Maltsev, "Estimation of morphological characteristics of single particles from light scattering data in flow cytometry," Russian Chemical Bulletin 43, 1115–1124 (1994)). The FLSI method employs a special optical scanning system which provides measurement of the intensity of the light scattered at polar angles from 10° to 120° and azimuthal angles from 0° to 180° from moving particles within a zone illuminated by a laser beam which is axial with the flow. The size of particles are calculated from the registered patterns on the basis of Mie scattering theory. This method provides much better signal to noise conditions than the ordinary forward scattering measurement as well as the precise determination of the size of the particles between 0.5 and 7 $\mu$m and this method is much more useful for sizing small particles than the ordinary forward scattering method.

Example of Embodiment and Performance of a Confocal Set-Up

The optical set-up and its performance as shown in FIG. 1 was tested. The light source (1) was a frequency doubled 10 mW CW Nd:YAG laser producing 300 $\mu$W beam at 532 nm wavelength. The illumination light was focused to the sample (3) through a microscope objective (2b) with numerical aperture of 0.5. The sample (3) was fed through a position-adjustable capillary tube (4) in conjunction with a simple liquid handling system. The emitted fluorescence light was separated from the illumination light by a dichroic mirror (5) and pinhole/aperture (6), and was detected by an avalanche photon counter (7)(EG&G Optoelectronics, Canada, type SPCM-141-AQ).

The set-up was tested in single-photon excitation confocal fluorescence mode with a test-sample containing E.coli bacteria stained with specific Rhodamine-B labelled antibodies at a predetermined concentration. The single photon bursts detected from the bacteria were Poisson distributed in the time domain with the mean expectation value of 6 counts. The background fluorescence and scattering from the optical components and the thermal noise of the detector occurred as random single counts at the rate of 200 c/s. Auto-correlating the signals with a threshold of 3 counts within 1 microsecond auto-correlation time resulted in 90% counting efficiency with an instrumental background of less than 1 count per 100 seconds.

The method and device of this invention is based on the use of correlation analysis of single photon bursts instead of the ordinary pulse height analysis. The use of correlation analysis has been made possible by providing a diffraction-limited focal volume and by the avalanche photon counters with very high quantum efficiency. The diffraction-limited focal volume applied in the device of this invention is substantially smaller than that in the ordinary flow cytometry. The significantly improved sensitivity and signal to background ratio is based on the fact that the fluorescent or scattering objects outside the focal volume do not contribute signals to the detector as in the case of ordinary flow cytometry. This means that the signals from free dye molecules in the sample flow are not coincident with the signals from the particles to be counted. Similarly, the background fluorescence of the optical components can not reach the detector because the point of origin of those photons is not confocal or is not two-photon excited.

It is obvious that the cuvette and fluidics system typical for the ordinary flow cytometry are one order of magnitude too rough for this application and a special liquid handling system and a cuvette with small dimensions may be necessary for reliable function of the system. Modern micromechanics methods allow microstructuring of glass, silicon or plastics for this purpose.

What is claimed is:

1. A flow fluorometric method wherein a signal from the fluorescent particles is obtained from a diffraction limited focal volume, comprising 1) providing a flow cytometer comprising a focal volume of excitation and a focal volume of detection which are (i) both located within a flow cuvette having a flow channel, and (ii) both smaller than a volume of the flow channel;

2) exciting a sample flowing within said flow cuvette so as to cause said sample containing fluorescent particles to emit a fluorescent signal;

3) detecting said fluorescent signal; wherein a) discrimination between background counts and counts from true fluorescent particles in the sample is based on auto-correlation analysis of single photon counts in the time domain or b) discrimination between the background counts and the counts from true fluorescent particles in the sample is based on cross-correlation analysis of the single photon counts from parallel detectors operating in the same or different spectral signal regions.

2. The method according to claim 1 wherein excitation of the fluorescent particles is performed with two-photon excitation.

3. The method according to claim 1 wherein excitation and detection is performed with a confocal optical set-up.

4. The method according to claim 1 wherein fluorescence emission is detected with one or more parallel photon counters capable of resolving single photons.

5. The method according to claim 4 wherein different photon counters have appropriate spectral filters tuned for different wavelength bands corresponding to different fluorescent dyes used to stain the particles.

6. The method according to claim 1 wherein the signals from parallel photon counters are both auto-correlated and cross-correlated.

7. A flow fluorometric method wherein a signal from the fluorescent particles is obtained from a diffraction limited focal volume, comprising 1) providing a flow cytometer;

2) exciting a sample flowing within a flow cuvette of said flow cytometer so as to cause said sample containing fluorescent particles to emit a fluorescent signal;

3) detecting said fluorescent signal; wherein a) discrimination between background counts and counts from true fluorescent particles in the sample is based on auto-correlation of analysis of single proton counts in the time domain or b) discrimination between the background counts and the counts from true fluorescent particles in the sample is based on cross-correlation analysis of the single photon counts from parallel detectors operating in the same or different spectral signal regions.

* * * * *

UNITED STATES PATENT AND TRADEMARK OFFICE
CERTIFICATE OF CORRECTION

PATENT NO. : 6,177,277 B1
DATED : January 23, 2001
INVENTOR(S) : Erkki Soini and Pekka Hänninen It is certified that error appears in the above-identified patent and that said Letters Patent is hereby corrected as shown below:

On title Page, under "(75) Inventor:" add the following co-inventor:

Pekka Hänninen, Tahvanankatu 9,
FIN-20400 Turku (FI)

Signed and Sealed this

Fifth Day of June, 2001

Attest:

Attesting Officer

NICHOLAS P. GODICI
*Acting Director of the United States Patent and Trademark Office*